United States Patent
Bax et al.

(10) Patent No.: US 10,507,092 B2
(45) Date of Patent: Dec. 17, 2019

(54) VIBRATION COMPENSATION SYSTEM FOR POWER TOOTHBRUSHES

(71) Applicant: KONINKLIJKE PHILIPS N.V., Eindhoven (NL)

(72) Inventors: Pieter Johannes Bax, Drachten (NL); Franciscus Jozef Bosman, Drachten (NL); Geert Hendrik Westrup, Drachten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 773 days.

(21) Appl. No.: 14/353,625

(22) PCT Filed: Oct. 12, 2012

(86) PCT No.: PCT/IB2012/055530
§ 371 (c)(1),
(2) Date: Apr. 23, 2014

(87) PCT Pub. No.: WO2013/061196
PCT Pub. Date: May 2, 2013

(65) Prior Publication Data
US 2014/0259473 A1    Sep. 18, 2014

Related U.S. Application Data

(60) Provisional application No. 61/550,578, filed on Oct. 24, 2011.

(51) Int. Cl.
*A61C 17/34* (2006.01)
*A61C 17/22* (2006.01)
(Continued)

(52) U.S. Cl.
CPC .............. *A61C 17/34* (2013.01); *A61C 17/20* (2013.01); *A61C 17/22* (2013.01); *A61C 17/225* (2013.01); *F16F 15/04* (2013.01)

(58) Field of Classification Search
CPC . A46B 13/00; A46B 2200/1066; A61C 17/34; A61C 17/22; A61C 17/20;
(Continued)

(56) References Cited

U.S. PATENT DOCUMENTS

| 5,378,153 A | 1/1995 | Giuliani |
| 6,859,968 B2 | 3/2005 | Miller et al. |

(Continued)

FOREIGN PATENT DOCUMENTS

| CN | 1703171 A | 11/2005 |
| DE | 1907693 A1 | 9/1969 |

(Continued)

*Primary Examiner* — Robert J Scruggs

(57) ABSTRACT

A power toothbrush having a vibration compensation system, the toothbrush including a toothbrush housing (72), and an actuator which includes a stator (74) having a first moment of inertia and a rotor (76) having a second moment of inertia, at the end of said rotor is mounted a bristle member. A first spring element (86) having a first spring constant connects the stator to the housing, while a second spring element (88) having a second spring constant connects the rotor to the housing, wherein the ratio of the first and second spring constants is substantially the same as the ratio of the first and second moments of inertia.

11 Claims, 6 Drawing Sheets

(51) Int. Cl.
*A61C 17/20* (2006.01)
*F16F 15/04* (2006.01)

(58) Field of Classification Search
CPC ... A61C 17/225; A61C 17/3481; A61C 17/32; A61C 17/222; A61C 17/349; A61C 17/3436; F61F 15/04; F16F 15/04
USPC .................. 15/22.1, 22.2, 167.1; 310/15, 36
See application file for complete search history.

(56) References Cited

U.S. PATENT DOCUMENTS

| | | | |
|---|---|---|---|
| 2004/0010871 A1* | 1/2004 | Nishinaka | A61C 17/3445 15/22.2 |
| 2006/0168745 A1 | 8/2006 | Kobayashi et al. | |
| 2006/0255665 A1* | 11/2006 | Kraus | H02K 33/18 310/36 |
| 2008/0028547 A1* | 2/2008 | Miller | A61C 17/3418 15/22.1 |
| 2010/0154151 A1* | 6/2010 | Grez | A61C 17/32 15/22.1 |
| 2011/0010874 A1 | 1/2011 | Dickie | |

FOREIGN PATENT DOCUMENTS

| | | |
|---|---|---|
| DE | 10355446 A1 | 6/2005 |
| EP | 2246009 A1 | 11/2010 |
| WO | 03092535 A2 | 11/2003 |

* cited by examiner $$C_\varphi = \frac{Ebh^3}{12\pi D_m n_w}$$

$$C_{ax} = \frac{Gb^2 h^2}{6.75 D_m^3 n_w}$$

VIBRATION COMPENSATION SYSTEM FOR POWER TOOTHBRUSHES

CROSS-REFERENCE TO PRIOR APPLICATIONS

This application is the U.S. National Phase application under 35 U.S.C. § 371 of International Application No. PCT/IB2012/055530, filed on Oct. 12, 2012, which claims the benefit of U.S. Provisional Patent Application No. 61/550,578, filed on Oct. 24, 2011. These applications are hereby incorporated by reference herein.

This invention relates generally to power toothbrushes, and more specifically concerns a system for decreasing vibration of a handle portion of the toothbrush during operation of the toothbrush.

Many power toothbrushes use a resonant drive system, so that they can run efficiently at frequencies which have proven effective in cleaning of teeth, e.g. in the range of 200-300 Hz. A resonant drive system typically comprises a mechanical mass/spring arrangement driven by an actuator. In operation, the resonant mass and spring exchange mechanical energy back and forth to produce a brushing force which is significantly larger than the actuator force itself.

However, if the stator portion of the actuator and/or the resonant spring within the handle are mechanically attached in any way to the housing of the toothbrush, such as for mounting purposes, the resulting reaction torque provided by the mass/spring action will act on the toothbrush housing, resulting in a vibration of the handle, the vibration being typically large enough to be noticeable and in some cases producing discomfort for the user, with at least some of the actuator energy being dissipated in the hand of the user.

Various solutions have been attempted to resolve or at least decrease this effect. One solution is to increase the mass moment of inertia of the housing (handle); however, due to the typically small diameter handles, any added mass to the handle will not significantly increase its mass moment of inertia. Hence there will be little effect on vibration by adding mass. Another solution is the use of a nodal spring arrangement, in which a spring is connected to the housing at a spring node. However, this arrangement is often structurally complex and further, the stator portion of the actuator is still connected to the handle, resulting in continuing vibration of the handle.

Accordingly, it is desirable to have a resonant drive arrangement to a power toothbrush which significantly reduces or eliminates vibration of the toothbrush handle during operation.

A vibration compensation system in a power toothbrush appliance, comprising; a toothbrush housing which is adapted to be grasped by a user; a power actuator for the toothbrush comprising a stator having a first moment of inertia and a rotor having a second moment of inertia, the rotor at a forward end thereof having mounted thereon a bristle member for cleaning the teeth, wherein the actuator in operation generates torque for driving the rotor and hence the bristle member, and wherein the stator and the rotor move in opposing directions during operation of the appliance; a first spring element or assembly having a first spring constant connecting the stator to the housing or an element fixed to the housing; and a second spring element having a second spring constant connected between the rotor and the housing or an element fixed to the housing, wherein the ratio of the first and second spring constants is sufficiently similar to the ratio of the first and second moments of inertia that there is substantially no resulting torque transmitted to the housing during operation of the toothbrush, and hence substantially no vibration of the housing during operation of the appliance.

Figure 1:
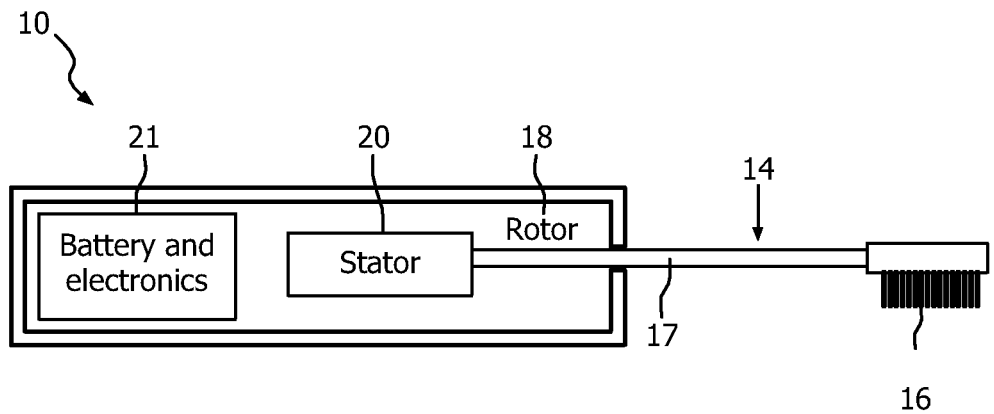
FIG. 1 is a cross-sectional view showing a simplified power toothbrush drive arrangement involving a stator and a rotor.

As discussed above, a conventional power toothbrush 10, shown in FIG. 1 with a resonant drive actuator system will include a handle 12 and a brushhead assembly 14, with a bristle portion 16 on the forward end thereof. The brushhead assembly 14 includes a spindle or neck member 17 which forms a rotor portion 18 of the actuator. The actuator also includes a stator portion 20. The stator is driven by a battery, with electronics control, shown generally together at 21. As indicated above, this arrangement results in a vibration being transmitted to the handle 12.

Figure 2:
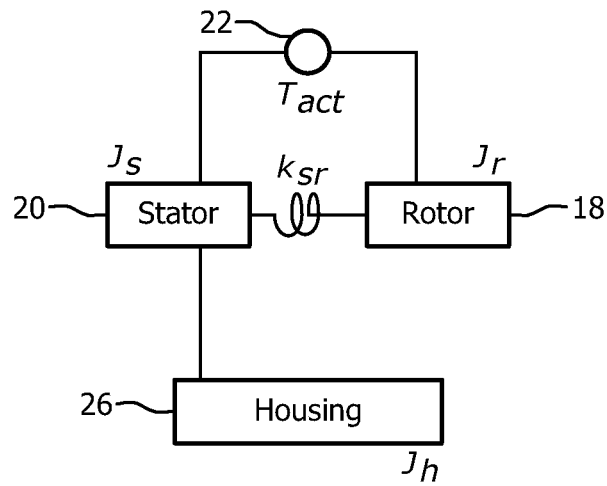
FIG. 2 is a diagram showing the various parts of the power toothbrush of FIG. 1 and the electrical and mechanical connections therebetween.
Figure 3:
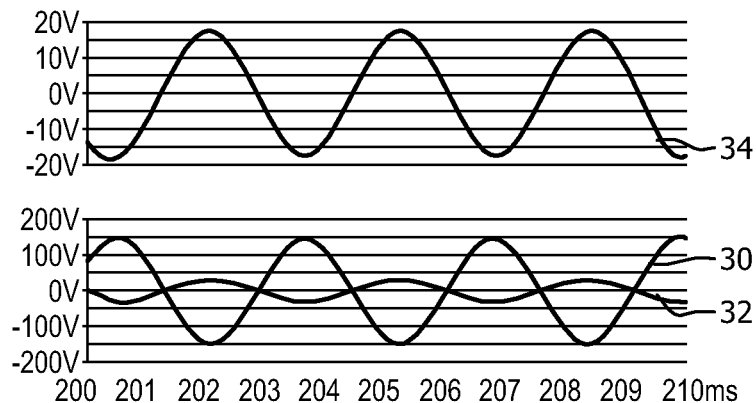
FIG. 3 is a diagram showing the movement of the housing, the stator and the rotor portions of FIG. 1, respectively.

The vibration effect for the actuator system of FIG. 1 is shown in FIGS. 2 and 3. FIG. 2 shows a source ($T_{act}$) of torque for actuator 22, driving the stator/rotor arrangement. Stator 20 has a mass moment of inertia $J_s$ while rotor 18 has a mass moment of inertia $J_r$. Rotor 18 is connected to the stator 20 by a spring 24, designated $k_{sr}$, which is the resilient part of the mass spring system of the resonant drive system, while the stator is mechanically connected to the housing 26, which has a mass moment of inertia $J_h$. $J_h$ includes the mass of the electronics and the battery, respectively, while $J_r$ also includes the mass of the bristle portion of the toothbrush.

In resulting operation, the rotor 18 oscillates with a frequency and an amplitude to produce a cleansing action on the teeth. Referring to FIG. 3, the vibration of the rotor (spindle) is shown at line 30 in FIG. 3, while the movement of the stator, designated at line 32, remains relatively quiet. Housing 26, however, experiences a significant vibration, as shown by line 34. The vibration of the rotor, with its relatively large amplitude, is 180° out of phase with the vibration of the housing 34, while the small vibration of the stator is in phase with the vibration of the housing.

Figure 4:
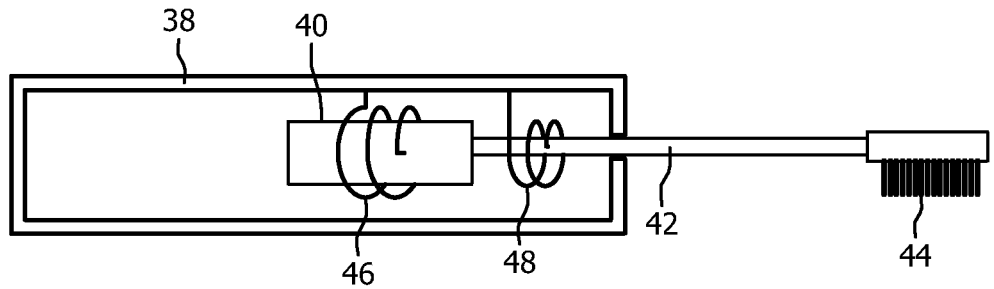
FIG. 4 is a diagram showing the drive arrangement described herein for reducing vibration of the handle during operation of the power toothbrush.

In the present arrangement, shown and described herein, the reaction of torque from the stator is compensated by a second reaction torque from the rotor. As indicated above, this is possible because the stator and the rotor move in operation in opposite directions. FIG. 4 shows a simplified representation of the present vibration compensation arrangement, including a housing (handle) 38, a stator 40, and a rotor 42, which includes a spindle, with a bristle portion 44 at the forward end thereof. A spring 46 is fixed (fixedly attached) to both the stator 40 and the housing (handle) 38, while a spring 48 is fixed between rotor 42 and the housing 38. The spring constants $K_{sh}$ and $K_{rh}$ of springs 46 and 48, respectively, are selected to have the same ratio as the mass moments of inertia of the stator and rotor, respectively. This results in the net torque on the housing being zero, i.e. no vibration to the housing.

Figure 5:
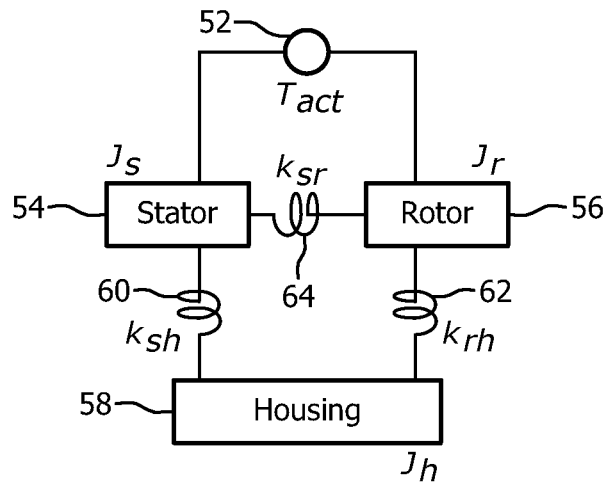
FIG. 5 is a diagram showing the connections between the elements of the drive arrangement of FIG. 4.

FIG. 5 is a schematic representation of the system of FIG. 4, including a source of torque 52, stator 54, rotor 56 and housing 58. Spring 60 connects the stator 54 and the housing 58, while spring 62 connects rotor 56 and the housing 58. Spring 64 connects the stator and the rotor. $J_s$, $J_r$ and $J_h$ represent the mass moments of inertia for the stator, rotor and housing while $k_{sh}$, and $k_{rh}$ represent the spring constants of springs 60 and 62. The rotor and the stator have opposing movements/oscillations; their respective torques therefore oppose each other relative to any action on the housing. In order to produce a net torque to the housing of approximately zero, such that there is little, if any, vibration of the handle, the ratio of the spring constants $$\frac{K_{RH}}{K_{SH}}$$

must approximately equal me ratio of the mass moments of inertia $$\frac{J_R}{J_S}.$$

Figure 6:
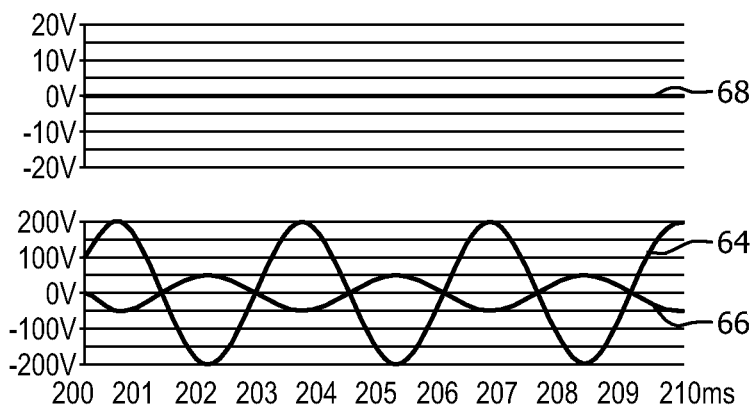
FIG. 6 is a vibration diagram showing the movement of the rotor, the stator and the housing portions with the arrangement described herein.

When the ratio of the spring constants equals the ratio of the mass moments of inertia, vibration of the handle is substantially zero, since the net torque applied to the handle will be zero. This is illustrated in FIG. 6, which shows rotor movement represented by line 64 and stator movement by line 66, opposite relative to the rotor. The result is a lack of vibration to the housing, as shown by line 68.

Figure 7:
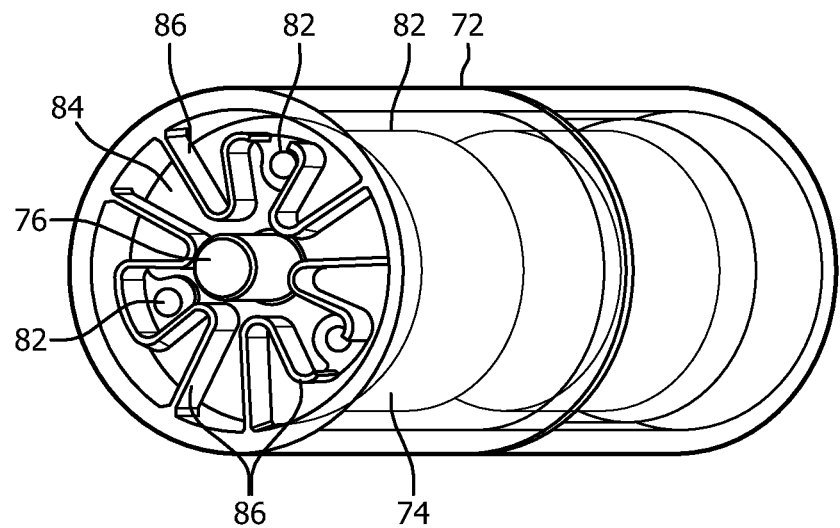
FIGS. 7 and 8 show schematic views of one embodiment of the present drive arrangement for a power toothbrush.
Figure 8:
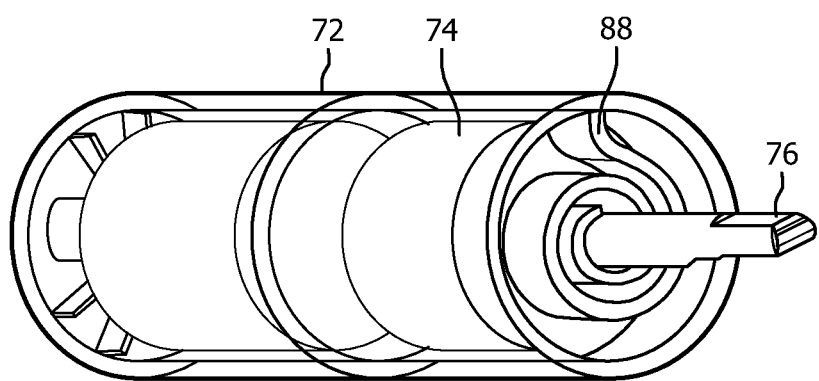

A first embodiment of the vibration compensation system is shown in FIGS. 7 and 8. The figures show a cylindrical housing 72, a stator 74 and a rotor 76. The stator and the rotor are selected to provide an effective rotation of a drive shaft or neck to which a bristle member is attached. FIG. 7 shows the spring connection between the stator and the housing. In this particular arrangement, three pin protrusions 82-82 extend out from the rear end surface 84 of the stator 74. The spring connection comprises three separate leaf springs 86-86, one associated with each pin. In the embodiment shown, the springs are plastic, although they could be metal as well. They are flexible, and are generally shaped in the form of a "W".

FIG. 8 shows the opposing end of the article, with the rotor portion of the actuator shown at 76. A spring 88 in the embodiment shown has a spiral shape and extends between the housing and the rotor, to both of which the spring is fixedly attached. The thickness of the spring is 0.3-0.4 mm if it is plastic. The spring would typically be thinner if it was made out of metal. The spring connections can be made in various ways, including welding or gluing, among others.

The two springs could also have an additional function. For instance, the stator spring may be a leaf spring, used as the suspension for the actuator within the housing, extending between the stator and the housing. The rotor (spindle) spring may be a leaf spring extending parallel with the housing between a member secured to the spindle and a protrusion extending a small distance inwardly from the housing.

Figure 9:
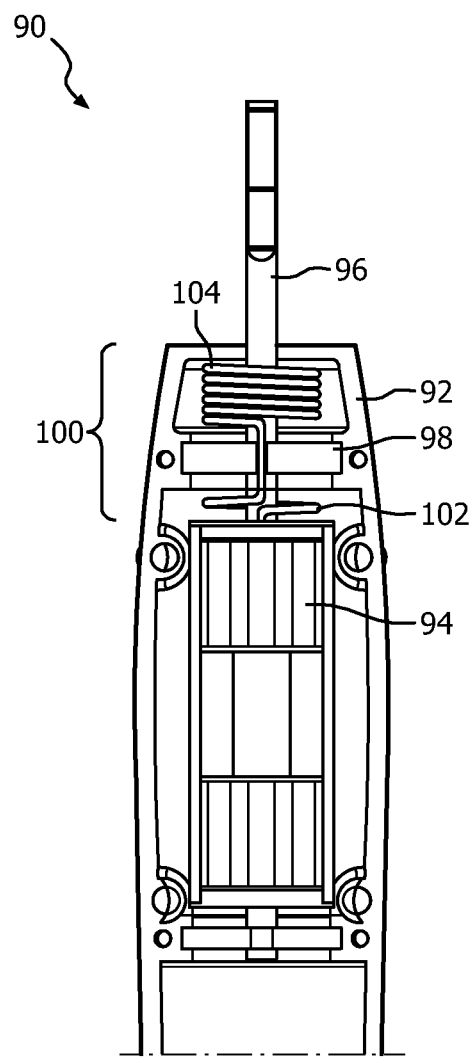
FIG. 9 shows a cut-away view of another embodiment of the present drive arrangement.

FIG. 9 shows a cut-away view of another embodiment, shown generally at 90. The embodiment includes a housing 92, a stator 94 and a rotor 96. At the end of the rotor a brushhead (not shown) is typically mounted. Rotor 96 extends from the stator through a mounting disc 98, which is mounted fixedly to the housing 92. In this embodiment, a single spring 100 accomplishes both the spring fixed connection between the stator and the housing and the rotor and the housing. The single spring extends from the stator 94, then a single turn section to a groove in mounting disc 98, then a five turn section to rotor 96. The single-turn section 102 of spring 100 functions as the stator spring, between the stator and the housing, while the five-turn section 104 functions as the rotor spring, between the rotor and the housing.

The important consideration again is that the ratio of the spring constants (ratio of the stator spring section 102 and the rotor spring section 104) is the same or approximately the same as the ratio of moments of inertia of the stator and rotor sections. This results in a net torque of zero to the housing.

While an exact ratio match will produce a zero net torque, the net torque remains close to zero over a range of spring constant ratios, i.e. the two ratios need not be identical to have the desired result of zero torque. The matched ratio arrangement is also not affected by load, i.e. use of the appliance on the teeth. Since under load there is no vibration transmitted to the handle, that portion of the actuation energy is applied to the teeth, resulting in additional energy for cleaning and resulting in improved efficiency of the toothbrush. Hence, the present matched ratio arrangement has a dual advantageous effect, i.e. it reduces/eliminates vibration of the handle, resulting in increased comfort for the user, and also increases the efficiency, i.e. the cleaning effectiveness, of the appliance.

Figure 11:
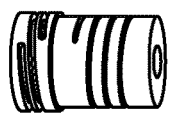
FIG. 11 shows a pictorial view of one of the variations of FIG. 10 and formulas of spring stiffness for axial and tangential directions.

In some arrangements, the stator must be able to move relative to the housing in both axial and tangential directions. In one design, the cross section of the spring windings is rectangular, with the windings in the two spring ends being oriented 90° to each other so that the single spring can be wound from one rectangular wire. Functionally, such a cross section provides another degree of freedom, enabling the stiffness in the tangential spring direction to be independent of the stiffness in the axial spring direction. According to FIG. 11, the axial stiffness correlates with $b^2 h^2$ so that the orientation of the cross-section of the windings is not relevant. The tangential stiffness, however, correlates with $bh^3$, so that a change in the orientation of the cross-section of the winding results in a change in the stiffness ratio of the spring. The axial stiffness and the tangential stiffness, respectively, can be scaled relative to each other, with the axial stiffness varying in accordance with diameter D, while the tangential stiffness varies with $D^3$. In this way, the axial spring stiffness and the tangential spring stiffness, combined with the mass and moment of inertia can be tuned to the desired resonance frequency ratio.

The axial and tangential stiffness ratio is determined from the ratio of each mass and moment of inertia, with the axial ratio being 1:2.5 and the tangential ratio being 1:10. The b/h ratio is 0.5. The total stiffness, together with the rotor mass/moment of inertia determines the resonant frequency in both directions.

Figures 10, 10A:
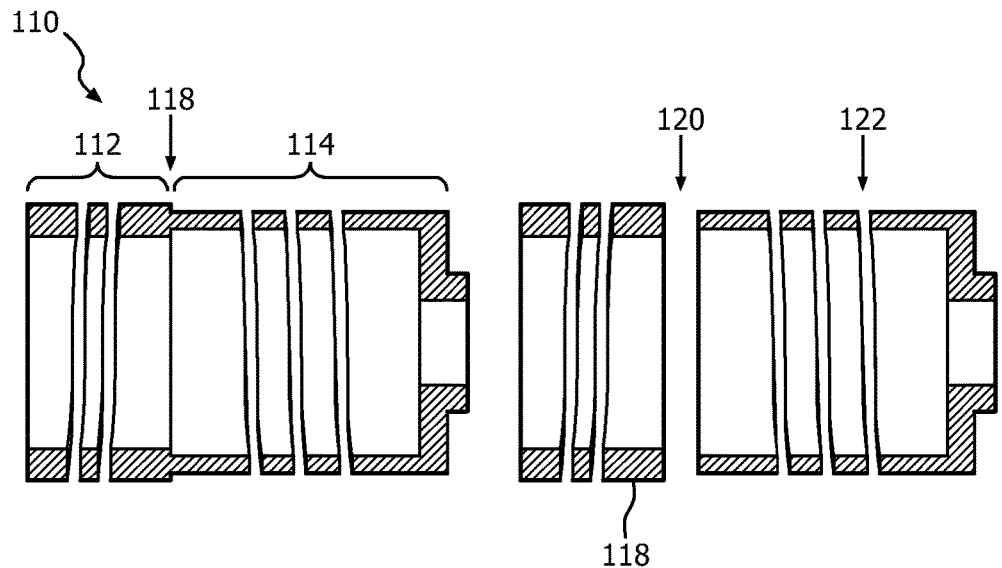
FIGS. 10 and 10A are cross-sectional diagrams showing two variations of a spring arrangement.

FIG. 10 shows a single spring 110 embodiment, where left side winding 112 (one winding) is connected to the stator while the right side winding 114 (2.5 windings), with the cross-section thereof being rotated 90°, is connected to the output shaft (not shown). The mid-portion 118 of the single spring 110 is connected to the housing (not shown). The winding arrangement of FIG. 10 can be separated into two pieces, (as shown in FIG. 10A). This arrangement enables a head/handle interface at a break point 120. With the replacement spring portion 122 being part of the brushhead assembly, spring portion 122 can be adjusted to accommodate other mass properties of the entire replacement part, while still giving the same vibration compensation effect when attached to the handle. The other spring portion 118 remains with the handle.

Figure 12:
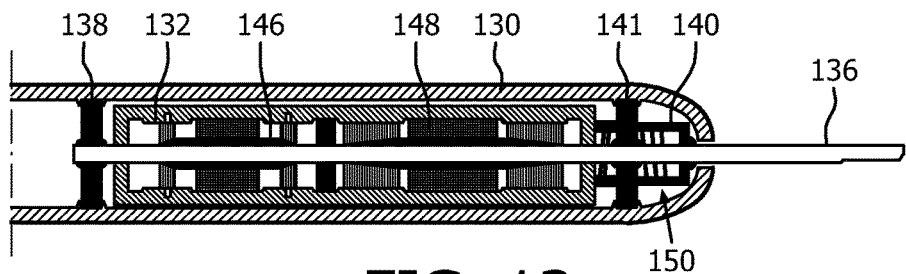
FIG. 12 is a cross-sectional diagram of a power toothbrush with actuator with a spring compensation assembly.

As indicated above, the actuator stator in some arrangements must be able to move relative to the housing in both axial and tangential directions. One specific arrangement is shown in FIG. 12. FIG. 12 includes a portion of a housing 130 of the appliance, an actuator stator 132 and a rotor/shaft 136 on which a brushhead assembly can be mounted. In this arrangement, the actuator is supported by bearings 138, 140 located outside both ends of the actuator, the bearings being connected to the housing 130. The bearings 138 and 140 carry the user load from the brush to the handle, bearing the brushing force applied by the user. The front bearing 140 is positioned in a circular mount 141 which is connected to the housing. The shaft 136 is supported by actuator bearings 146 and 148. The spring suspension assembly connecting the stator and the rotor to the housing is represented at 150.

Figure 13:
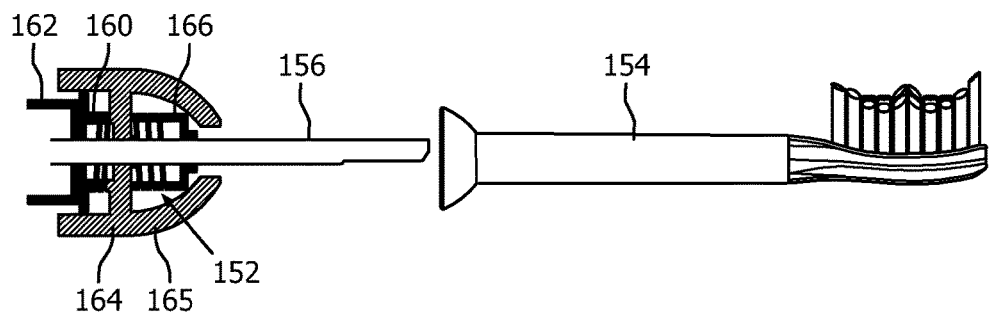
FIG. 13 is a cross-sectional diagram of a portion of a power toothbrush with one spring compensation system.
Figure 14:
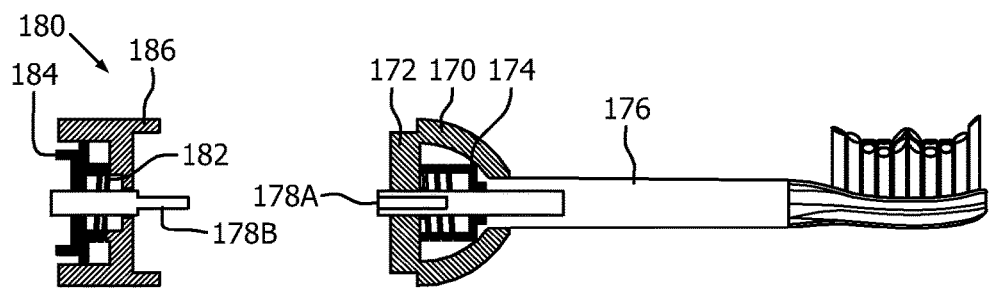
FIG. 14 is a cross-sectional diagram of a portion of a power toothbrush with another spring compensation system.

FIGS. 13 and 14 show in more detail the spring assembly system. In the embodiment of FIG. 13, the spring assembly 152 is arranged so that the brushhead assembly 154 is simply fitted onto and removed from shaft 156. Spring portion 152 is unitary, connected in one part 160 to stator 162 and housing 164 through fixed mount element 165, while the other spring part 166 is connected to the rotor 156 and the housing 164 through mount element 165.

FIG. 14 shows an alternative arrangement, wherein the forward end 170 of the housing and fixed housing mount 172, containing a spring section 174 and a brushhead assembly 176, is detachable from the remainder 180 of the appliance through a connection interface 178A and 178B. A spring section 182 connects the stator 184 to the housing mount 186.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A vibration compensation system for a power toothbrush appliance, comprising;
    a housing which is adapted to be grasped by a user;
    an actuator that comprises a stator having a first moment of inertia and a rotor having a second moment of inertia, the rotor at a forward end thereof having mounted thereon a bristle member for cleaning the teeth, wherein the stator surrounds at least a portion of the rotor, wherein the actuator in operation generates torque for driving the rotor and hence the bristle member, and wherein the stator and the rotor are configured to move in opposing directions during operation of the power toothbrush appliance; and
    a spring arrangement comprising:
        a first spring element or assembly connected between and fixedly attached to both the stator and the housing or an element fixed to the housing, wherein the first spring element has a first spring constant; and
        a second spring element connected between and fixedly attached to both the rotor and the housing or an element fixed to the housing, wherein the second spring element has a second spring constant, wherein the ratio of the first and second spring constants is approximately equal to the ratio of the first and second moments of inertia that there is substantially no resulting torque transmitted to the housing during operation of the power toothbrush appliance, and hence substantially no vibration of the housing during operation of the power toothbrush appliance,
        wherein the first and second spring elements comprise a single spring, wherein the single spring is connected to the housing or an element connected to the housing at a selected point between the first and second spring elements, and
        wherein the first and second spring elements are disconnectable from each other, further wherein the second spring element is part of an assembly which includes a distal portion of the housing, a brushhead assembly and an interface part which connects with an interface part on a remainder of the appliance.

2. The system of claim 1, wherein the ratio of the first and second spring constants is substantially the same as the ratio of the first and second moments of inertia.

3. The system of claim 1, wherein the single spring is a coil spring.

4. The system of claim 1, wherein the first spring element or assembly comprises a plurality of flat springs, while the second spring element or assembly is a spiral spring.

5. The system of claim 1, wherein one or both of the first and second spring elements or assemblies are plastic.

6. The system of claim 1, wherein one or both of the first and second spring elements or assemblies are metal.

7. The system of claim 1, wherein the first and second spring elements are arranged to permit both axial and tangential movement of the stator relative to the housing while maintaining the compensation for vibration.

8. A power toothbrush appliance, comprising:
    a handle with a first toothbrush housing portion containing an actuator which includes a stator having a first moment of inertia, and a handle rotor portion, wherein the stator surrounds at least a portion of the handle rotor portion, wherein the actuator in operation generates torque for driving the handle rotor portion, and wherein the stator and the handle rotor portion are configured to move in opposing directions during operation of the appliance; and
    a brushhead assembly, comprising a brushhead shaft having a bristle member at a distal end thereof for cleaning of teeth, and a brushhead rotor portion with a connecting rotor interface portion at a proximal end thereof for removably connecting the brushhead rotor portion to the handle rotor portion, wherein the handle rotor portion and the brushhead rotor portion form an appliance rotor having a second moment of inertia;

a second toothbrush housing portion configured to couple with the first toothbrush housing portion in response to the brushhead assembly being connected to the handle, the first and second toothbrush housing portions defining an appliance housing; and a spring arrangement comprising:

a first spring element or assembly connected between and fixedly attached to both the stator and the first housing portion or element fixed to the housing, wherein the first spring element has a first spring constant; and a second spring element or assembly having a second spring constant connected between and fixedly attached to both the brushhead rotor portion and the second housing portion or an element fixed to the second housing portion, wherein the second spring element has a second spring constant, further wherein the first and second spring elements are disconnectable from each other, wherein a ratio of the first and second spring constants approximately equal to a ratio of the first and second moments of inertia that responsive to the brushhead assembly being connected to the handle, there is substantially no resulting torque transmitted to the appliance housing during operation of the power toothbrush appliance and hence substantially no vibration of the appliance housing during operation of the power toothbrush appliance.

9. The power toothbrush appliance of claim 8, wherein the ratio of the first and second spring constants is substantially the same as the ratio of the first and second moments of inertia.

10. The power toothbrush appliance of claim 8, wherein the second spring element or assembly is plastic.

11. The power toothbrush appliance of claim 8, wherein the second spring element or assembly is metal.

* * * * *